United States Patent [19]

Koyano et al.

[11] 3,950,436

[45] Apr. 13, 1976

[54] PROCESS FOR PREPARING VICINAL DIALKOXYALKANES

[75] Inventors: Takashi Koyano, Ohimachi; Saburo Fukushi, Tokyo, both of Japan

[73] Assignee: Toa Nenryo Kogyo Kabushiki Kaisha, Tokyo, Japan

[22] Filed: May 10, 1974

[21] Appl. No.: 468,639

Related U.S. Application Data

[63] Continuation of Ser. No. 260,522, June 7, 1972, abandoned, which is a continuation-in-part of Ser. No. 845,542, July 28, 1969, Pat. No. 3,699,174, which is a continuation-in-part of Ser. No. 691,151, Dec. 18, 1967, abandoned.

[30] Foreign Application Priority Data

Feb. 8, 1967 Japan.................................. 42-8098

[52] U.S. Cl............................................... 260/615 R
[51] Int. Cl.$^2$.................... C07C 41/10; C07C 41/00
[58] Field of Search............................... 260/615 R

[56] References Cited
UNITED STATES PATENTS

| 1,459,177 | 6/1923 | Carter | 260/615 R |
|---|---|---|---|
| 1,941,108 | 12/1933 | Reppe | 260/615 R X |
| 2,042,219 | 5/1936 | Groll et al. | 260/615 R X |
| 2,148,437 | 2/1939 | Coleman et al. | 260/615 R |
| 2,332,467 | 10/1943 | Linn et al. | 260/614 |
| 2,426,863 | 9/1947 | Deebel | 260/615 R |
| 3,699,174 | 10/1972 | Koyano et al. | 260/615 R |

OTHER PUBLICATIONS

Remp, Soc. Chim. de France, Bull. 24 (1957) 844–847.

Koyano et al., Kogyo Kagaku Zasshi (1971) 74(2) 203–207 Japan.

*Primary Examiner*—Howard T. Mars
*Attorney, Agent, or Firm*—Woodhams, Blanchard and Flynn

[57] ABSTRACT

A process is disclosed for preparing vicinal dialkoxyalkanes by reacting a vicinal dihaloalkane with an alkanol in the presence of a hydrogen halide absorbing agent which is substantially insoluble in the alkanol.

6 Claims, No Drawings

PROCESS FOR PREPARING VICINAL DIALKOXYALKANES

This application is a continuation of our copending application Ser. No. 260,522, filed June 7, 1972, now abandoned which in turn is a continuation-in-part of Ser. No. 845,542, filed July 28, 1969, now U.S. Pat. No. 3,699,174, which in turn is a continuation-in-part of Ser. No. 691,151, filed Dec. 18, 1967, now abandoned.

BACKGROUND OF THE INVENTION

This invention relates to a process for preparing dialkoxyalkanes, particularly to a process for preparing vicinal dialkoxyalkanes from vicinal dihaloalkanes and alkanols.

DESCRIPTION OF THE PRIOR ART

The generally known processes for preparing dialkoxyalkanes have comprised reacting an alkyl bromide with the sodium salt of ethylene glycol in glycol solvent (Ind. & Eng. Chem. 18, 669–675 (1926)), methylating the sodium salt of methyl cellosolve with methyl chloride or dimethylsulfate (J. Amer. Chem. Soc. 67, 1615 (1945) and 60, 1714 (1938)) and reacting a dihaloalkane with a sodium alcoholate in the liquid phase (Bull. Soc. Chim. France 1957, pp. 844–847).

The first two prior processes are not satisfactory from the economic point of view, because they require expensive reagents and plural reaction steps. Dialkoxyalkanes that are obtained by the third process are compounds having relatively long chains, such as 1,6-dipropoxyhexane, 1,6-dibutoxyhexane, 1,6-dilauroxyhexane, etc. With regard to the preparation of 1,2-dialkoxyethanes by the reaction of 1,2-dihaloethanes with sodium alcoholates, there is disclosed in said publication only the production of 1,2-dilauroxyethane in yield not sufficient for industrial purposes. In the reaction of a vicinal dihaloethane with an alkali metal short chain alcoholate, such as lithium, sodium or potassium alcoholate, the dehydrohalogenation reaction of the dihaloethane takes place prior to the desired substitution reaction because of the strong basicity of the alkali metal alcoholate and there are formed products such as vinyl halide, vinyl alkyl ether, etc. Thus, when the dihaloalkanes have short chains, such as dihaloethanes, it is impossible to form dialkoxyethanes by substituting the halogens with short chain alkoxy groups because the dehydrohalogenation reaction predominates.

1,2-dimethoxyethane (glyme) has been recognized in the field of organic synthetic chemistry as an ether solvent miscible with water and having an excellent solubility, and the demand for it has increased. Dihaloalkanes can be obtained in the petroleum chemistry industry abundantly and at a low cost. Although dialkoxyalkanes can be obtained by the direct reaction of dihaloalkanes with aliphatic alcohols, hydrogen halides are generated in the reaction and these severely corrode the reaction apparatus and cause side reactions whereby the yields of the final products are lowered and the recovery of alcohols is reduced.

The Williamson reaction for the synthesis of ethers relates to the reaction of an alkanol (ROH) with an organic halide (RX) in the presence of an alcohol-soluble base such as sodium hydroxide. The reaction takes place between the alkoxide, formed between the alkanol and the base (Na$^+$OR$^-$), and the halide (RX). This reaction can be represented by the following reaction formula. Refer to Kirk-Othmer, Enclyclopedia of Chemical Technology, Second Edition, Vol. 8. page 474 (1965).

The action of the soluble base in said reaction is to produce RO$^-$ ion having a great nucleophilicity by the following eqation.

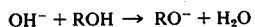

Accordingly, said reaction is a $S_N2$ reaction in which the RO$^-$ ion attacks R'X and it proceeds at a temperature of about 100°C. or below. However, when a vicinal dihaloalkane is used as a starting material for the preparation of a vicinal dialkoxyalkane (the desired product of the present invention), the elimination reaction will occur by the attack of RO$^-$ in advance of the substitution reaction, which makes it impossible to prepare a vicinal dialkoxyalkane.

These facts will be verified by experimental data below. The Williamson type reaction conditions applied to 1,2-dichloroethane as a starting material is well known in the art as a vinyl chloride synthesis method. Refer to Kirk-Othmer, Encyclopedia of Chemical Technology, First Edition, Vol. 14, page 723 (1955).

SUMMARY OF THE INVENTION

According to the invention, the detrimental effect of hydrogen halides of (1) causing dehydrated (unsaturated) by-products and of (2) causing corrosion of the equipment, is overcome, and the reaction of vicinal ether formation is caused to proceed satisfactorily by carrying out the reaction in the presence of hydrogen halide absorbing agents insoluble in the alcohols, namely, metals and metal compounds capable of deactivating the hydrogen halide as it is formed and removing it from the reactant mixture promptly.

As thus carried out, the process of this invention differs critically from any of the above-noted prior reactions, particularly the Williamson type reaction. That is to say, the present invention relates to a process for synthesizing vicinal dialkoxyalkanes (dialkoxyalkanes having the two alkoxy radicals on adjacent carbon atoms) from vicinal dihaloalkanes (dihaloalkanes having the two halogens on adjacent carbon atoms) as the starting material, by a direct reaction in the liquid phase with alkanols, as shown in the following equation:

wherein R is an alkylene radical of 2 to 4 carbon atoms substituted by two vicinal halogens X, and R' is an alkyl group of from 1 to 4 carbon atoms.

For example, 1,2-dialkoxyethane is synthesized from 1,2-dichloroethane by the reaction of 1,2-dichloroethane and an alkanol, as shown in the following equation:

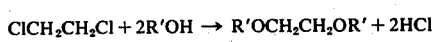

In this case, since the nucleophilic property of R'OH is small, a high reaction temperature of about 200°C. is required, but, on the other hand, since the basicity of R'OH is small, the elimination reaction of halogen will not take place and the substitution reaction will proceed at a satisfactory yield. However, without more, the hydrogen chloride produced here will act as a catalyst for the dehydration reaction of the alkanol and also will react with the produced dialkoxyethane to decompose the latter. Therefore, it is necessary to deactivate the hydrogen chloride and remove the same out of the system promptly. For this purpose, the said reaction is carried out in the presence of an insoluble base (such as $Mg(OH)_2$, $CaCO_3$, $ZnO$) or a reactive metal (Fe) according to the present invention.

The hydrogen halide absorbing agents used in the present invention are metals and metallic compounds insoluble in alcohols as mentioned above, and selected from the group consisting of metallic iron, zinc oxide, zinc hydroxide, magnesium oxide, magnesium hydroxide, magnesium alkoxide in which the alkyl group is one to four carbon atoms, calcium oxide, calcium hydroxide and calcium carbonate.

The vicinal dihaloalkane, which can be written X-R-X, has the two halogen atoms (X) respectively attached to adjacent carbon atoms in the molecule. Preferred examples are 1,2-dichloroethane, 1,2-dibromoethane, 1,2-dichloropropane, 1,2-dibromopropane, 1,2-dichlorobutane, 1,2-dibromobutane, 2,3-dichlorobutane, and 2,3-dibromobutane. The halogen (X) is preferably chlorine or bromine, as seen from the foregoing.

The alkanol reactant, R'OH, is illustrated by methanol, ethanol, n-butanol, n-propanol, i-butanol and i-propanol.

The amount of the hydrogen halide absorbing agent used is selected to be in the range of from one to five equivalents per equivalent of the hydrogen halide which will theoretically be formed from the dihaloalkane.

The operating temperature for the process of the invention is in the range of 100° to 350°C., preferably, 150° to 250°C. At a temperature above 350°C., dehydrohalogenation occurs, while at temperatures below 100°C., the velocity of the reaction is so slow that the yield is reduced and the practical value of the process becomes relatively low. The reaction pressure is not critical, and the reaction can be carried out at atmospheric or elevated pressure. Exemplary is the autogenous pressure of a sealed reaction zone, although this is not necessary.

The time period or duration of the reaction will, of course, depend on the temperature, pressure, and specific reactants. The metal halides, which are a result of the sequestering reaction of the hydrogen halide absorbing agents heretofore mentioned, can be separated by conventional methods, as by distillation.

In carrying out the process of the invention, any of the conventional batch or continuous systems can be employed. As a preferred procedure, there can be mentioned a process wherein the dihaloalkane is brought into contact with the alkanol while stirring or agitating the reaction mixture, while heating the same, in the presence of any of the abovenamed hydrogen halide absorbing agents. In an industrial apparatus, either a fixed bed process or a fluidized process can be employed, according to the physical state of the hydrogen chloride absorbing agent that is used.

The ratio of the amounts of dihaloalkane and alkanol used can be the stoichiometric ratio, namely, one mole of the former per two moles of the latter. However, in view of the tendency for the conversion to increase as the relative amount of the alkanol is increased, it is preferable in carrying out the process of this invention to use more than two moles of alkanol per one mole of dihaloalkane. Generally, the amount of alkanol used is in the range of two to ten moles per one mole of dihaloalkane.

The reaction is preferably carried out in a sealed vessel, and the course of the reaction can readily be followed using such analytical methods as gas chromatography.

DESCRIPTION OF THE PREFERRED EMBODIMENTS

Example 1

Into a sealable 50 ml. glass tube were charged 0.06 moles of the metallic compound according to this invention, 0.05 moles of dehydrated, pure 1,2-dichloroethane and 25 ml. of methanol. The tube was sealed under a nitrogen atmosphere. The tube was maintained at 200°C. for 6 hours while undergoing shaking. After cooling, the reaction products were taken out and analyzed by gas chromatography and the results as listed in Table 1 were obtained.

For comparison, the results obtained by reactions carried out under the same conditions as above, except that no metallic compound was present in the reaction system, are also listed. It was found that effects obtained by the presence of metallic compounds according to the process of the present invention are remarkable.

The velocity of the reaction carried out in a sealed tube will be somewhat lower than that in an autoclave, due to the inferior reaction efficiency resulting from the stirring procedure.

Table 1

| Metallic compound | 1,2-dichloroethane conversion (%) | 1,2-dimethoxyethane selectivity (%) | (yield %) | 2-chloroethyl methyl ether selectivity (%) (note 1) |
|---|---|---|---|---|
| None | 50.0 | 24.6 | (12.3) | 46.9 |
| Zinc oxide | 100.0 | 65.9 | (65.9) | 0 |
| Magnesium oxide | 84.1 | 65.3 | (54.9) | 21.9 |
| Calcium oxide | 91.6 | 46.0 | (42.1) | 12.2 |

(Note 1) 2-chloroethyl methyl ether is the intermediate product of 1,2-dimethoxyethane, and can be converted into the latter.

Example 2

Into a 500 ml. stainless steel autoclave were placed 0.6 moles of zinc hydroxide, 0.5 moles of 1,2-dichloroethane and 200 ml. of methanol. A nitrogen atmosphere was used and after sealing the autoclave, the contents were reacted, while being stirred, at 200°C. for six hours. The analysis of the products revealed 1,2-dichloroethane conversion 96.7%, 1,2- dimethoxyethane selectivity 73.5% (yield 71.1%) and 2-chloroethyl methyl ether selectivity zero.

Example 3

Into a 200 ml. stainless steel autoclave were placed 7.0 g. of magnesium hydroxide and the inside of the autoclave was purged three times with nitrogen gas. 10.1 g. of refined anhydrous dichloroethane and 80 ml. of anhydrous methanol were introduced into the autoclave. After closing the autoclave, the contents were maintained at 200°C. with stirring for six hours and the reaction product was collected after cooling. Seven grams (yield 76%) of 1,2-dimethoxyethane were obtained. Hydrogen chloride was not detected in the product and the presence of metal due to the dissolution of the inner wall of the autoclave was almost undetectable.

Example 4

When 13.5 g. of iron powder, 9.9 g. of dichloroethane and 80 ml. of anhydrous methanol were used to carry out the reaction under the same conditions as described in Example 3, 6.6 g. (yield 73%) of 1,2-dimethoxyethane were obtained.

Example 5

Magnesium methylate was prepared as described below in a 200 ml. stainless steel autoclave. Into this were added 9.9 g. of dichloroethane under a stream of nitrogen. After closing the autoclave, the mixture was kept at 220°C. with stirring for 6 hours, and then cooled. The reaction product was collected and shown to be 1,2-dimethoxyethane (5.6 g. – yield 62%) by analysis.

In preparing the above-mentioned magnesium methylate, 4.0 g. of magnesium ribbons were washed with dilute hydrochloric acid and then with water and their surfaces were polished after drying. The ribbons were then placed in the autoclave, and 80 ml. of methanol were added under nitrogen. The mixture was kept at 100°C. for an hour and then cooled to room temperature. Hydrogen was drawn off, and the resulting magnesium methylate was subjected to the reaction with dichloroethane.

Example 6

The procedure of Example 1 was followed, except that the particular reactants and hydrogen halide absorbing agents were used as indicated below. The following results were obtained.

Table 2

| Process of the Present Invention | | | | | | | |
|---|---|---|---|---|---|---|---|
| Dihaloalkane | Alcohol | Hydrogen chloride absorbing agent | 1,2-dihaloalkane conversion (%) | 1,2-dialkoxyalkane | | Monosubstituted intermediate product | |
| | | | | selectivity (%) | yield (%) | selectivity (%) | yield (%) |
| 1,2-dichloroethane | methanol | Ca(OH)$_2$ | 92.0 | 47.5 | 41.0 | 11.5 | 10.6 |
| 1,2-dichloroethane | methanol | CaCO$_3$ | 76.7 | 62.5 | 48.0 | 27.1 | 20.8 |
| 1,2-dibromoethane | butanol | ZnO | — | — | 79.7 | — | — |
| 2,3-dichlorobutane | methanol | Mg(OH)$_2$ | 55.0 | — | 30.0 | — | 25.0 |
| 1,2-dichlorobutane | methanol | Mg(OH)$_2$ | 64.0 | — | 38.1 | — | 26.7 |

Example 7

When 7.0 g. of magnesium hydroxide, 9.8 g. of dichloroethane and 80 ml. of anhydrous methanol were kept at 180°C. for 18 hours in the same procedure as described in Example 3, 5.55 g. (yield 62%) of 1,2-dimethoxyethane and 1.17 g. of β-chloroethyl methyl ether were obtained.

Example 8

To illustrate the unobvious nature of the results obtainable from this invention, a series of experiments were carried out by the procedure of Example 1, except that the hydrogen halide absorbing agent was replaced by the soluble base as listed in Table 4. The results are as follows.

Table 4

| Base | 1,2-dichloroethane conversion (%) | 1,2-dimethoxyethane | |
|---|---|---|---|
| | | selectivity | yield |
| NaOH (Equivalent to NaOCH$_3$) | 100 | 0 | 0 |
| Na$_2$CO$_3$ | 96 | Trace | Trace |
| NaHCO$_3$ | 93 | Trace | Trace |
| KOH | 100 | 0 | 0 |
| K$_2$CO$_3$ | 99 | Trace | Trace |
| KHCO$_3$ | 97 | Trace | Trace |
| SrO | 96 | 18 | 17 |

Note) These experiments were carried out according to the process described in Example 1 of this application.

The failure to produce dialkoxyalkane under these conditions can be explained, as noted above, by the dehydrating action on the ethers as soon as it is formed in the reaction mixture.

The embodiments of the invention in which an exclusive property or privilege as claimed are defined as follows:

1. A process for synthesizing a dialkoxyalkane having the alkoxy radicals on adjacent carbon atoms, which comprises:

reacting at a temperature in the range of 100° to 350°C,
A. a dihaloalkane selected from the group consisting of dichloroalkanes and dibromoalkanes, said dihaloalkane having the halogen substituents on adjacent carbon atoms and having a total number of carbon atoms from 2 to 4, with,
B. an alkanol having 1 to 4 carbon atoms,
in the presence of from one to five equivalents, based on the halogen of the dihaloalkane, of metallic iron, as a hydrogen halide absorbing agent insoluble in said alkanol.

2. A process for synthesizing a dialkoxyalkane having the alkoxy radicals on adjacent carbon atoms, which consists of:

reacting at a temperature in the range of 100° to 350+°C, a reaction mixture consisting of
A. a dihaloalkane selected from the group consisting of dichloroalkanes and dibromoalkanes, said dihaloalkane having the halogen substituents on adjacent carbon atoms and having a total number of carbon atoms from 2 to 4, and, B. an alkanol having 1 to 4 carbon atoms, in the presence of from one to five equivalents, based on the halogen of the dihaloalkane, of zinc oxide or zinc hydroxide, as a hydrogen halide absorbing agent insoluble in said alkanol.

3. A process for synthesizing a dialkoxyalkane having the alkoxy radicals on adjacent carbon atoms, which consists of:

reacting at a temperature in the range of 100° to 350°C, a reaction mixture consisting of, A. a dihaloalkane selected from the group consisting of dichloroalkanes and dibromoalkanes, said dihaloalkane having the halogen substituents on adjacent carbon atoms and having a total number of carbon atoms from 2 to 4, and, B. an alkanol having 1 to 4 carbon atoms, in the presence of from one to five equivalents, based on the halogen of the dihaloalkane, of magnesium oxide or magnesium hydroxide, as a hydrogen halide absorbing agent insoluble in said alkanol.

4. A process for synthesizing a dialkoxyalkane having the alkoxy radicals on adjacent carbon atoms, which consists of:

reacting at a temperature in the range of 100° to 350°C, a reaction mixture consisting of A. a dihaloalkane selected from the group consisting of dichloroalkanes and dibromoalkanes, said dihaloalkane having the halogen substituents on adjacent carbon atoms and having a total number of carbon atoms from 2 to 4, and, B. an alkanol having 1 to 4 carbon atoms, in the presence of from one to five equivalents, based on the halogen of the dihaloalkane, of calcium oxide or calcium hydroxide, as a hydrogen halide absorbing agent insoluble in said alkanol.

5. A process for synthesizing a dialkoxyalkane having the alkoxy radicals on adjacent carbon atoms, which consists of:

reacting at a temperature in the range of 100° to 350°C, a reaction mixture consisting of A. a dihaloalkane selected from the group consisting of dichloroalkanes and dibromoalkanes, said dihaloalkane having the halogen substituents on adjacent carbon atoms and having a total number of carbon atoms from 2 to 4, and, B. an alkanol having 1 to 4 carbon atoms, in the presence of from one to five equivalents, based on the halogen of the dihaloalkane, of calcium carbonate, as a hydrogen halide absorbing agent insoluble in said alkanol.

6. A process for synthesizing a dimethoxyalkane having the methoxy radicals on adjacent carbon atoms, which consists of:

reacting at a temperature in the range of 100° to 350°C, a reaction mixture consisting of A. a dihaloalkane selected from the group consisting of dichloroalkanes and dibromoalkanes, said dihaloalkane having the halogen substituents on adjacent carbon atoms and having a total number of carbon atoms from 2 to 4. and, B. magnesium methylate in methanol.

* * * * *

UNITED STATES PATENT AND TRADEMARK OFFICE
CERTIFICATE OF CORRECTION

PATENT NO. : 3 950 436
DATED : April 13, 1976
INVENTOR(S) : Takashi Koyano et al It is certified that error appears in the above-identified patent and that said Letters Patent are hereby corrected as shown below:

Column 6, line 65; change "350+C" to ---350°C---.

Column 8, line 30; change "2 to 4. and," to ---2 to 4,---.

Signed and Sealed this

Tenth Day of August 1976

[SEAL]

Attest:

RUTH C. MASON
*Attesting Officer*

C. MARSHALL DANN
*Commissioner of Patents and Trademarks*